(12) United States Patent
Schopke

(10) Patent No.: US 10,331,856 B1
(45) Date of Patent: Jun. 25, 2019

(54) PHYSICAL THERAPY PATIENT TREATMENT MONITORING SYSTEMS AND METHODS

(71) Applicant: One Call Care Management, Parsippany, NJ (US)

(72) Inventor: Patrick Michael Schopke, Tampa, FL (US)

(73) Assignee: One Call Care Management, Parsippany, NJ (US)

( * ) Notice: Subject to any disclaimer, the term of this patent is extended or adjusted under 35 U.S.C. 154(b) by 394 days.

(21) Appl. No.: 14/132,842

(22) Filed: Dec. 18, 2013

Related U.S. Application Data

(60) Provisional application No. 61/739,251, filed on Dec. 19, 2012, provisional application No. 61/761,296, filed on Feb. 6, 2013.

(51) Int. Cl.
*G06F 19/00* (2018.01)

(52) U.S. Cl.
CPC .................. *G06F 19/3418* (2013.01)

(58) Field of Classification Search
CPC ..... G06Q 50/22; G06Q 50/24; G06F 19/3418
See application file for complete search history.

(56) References Cited

U.S. PATENT DOCUMENTS

| | | | | |
|---|---|---|---|---|
| 8,332,234 B1* | 12/2012 | Armentano et al. | | 705/2 |
| 8,358,771 B1* | 1/2013 | Moore | | H04M 3/5158 |
| | | | | 379/265.01 |
| 2002/0133502 A1* | 9/2002 | Rosenthal | | G06F 19/3418 |
| 2003/0050566 A1* | 3/2003 | Ujhelyi et al. | | 600/515 |
| 2005/0090372 A1* | 4/2005 | Burrows et al. | | 482/8 |
| 2006/0008073 A1* | 1/2006 | Yoshizawa | | H04M 3/5158 |
| | | | | 379/266.07 |
| 2012/0100108 A1* | 4/2012 | Bartel et al. | | 424/93.3 |
| 2012/0130751 A1* | 5/2012 | McHugh | | G06Q 40/08 |
| | | | | 705/4 |
| 2013/0085780 A1* | 4/2013 | Braunstein | | G06Q 50/24 |
| | | | | 705/3 |
| 2014/0348318 A1* | 11/2014 | Talapady | | H04M 3/5191 |
| | | | | 379/265.09 |

* cited by examiner

*Primary Examiner* — Eliza A Lam
(74) *Attorney, Agent, or Firm* — Eric L. Sophir; Dentons US LLP

(57) ABSTRACT

The physical therapy treatment systems and methods described herein include an active utilization management (UM) program that can monitor the clinical efficacy of outpatient rehabilitation, including on-going physical therapy or occupational therapy. When a treating physician submits a claim, the systems and methods described herein can automatically apply a guideline for monitoring the pace of treatment and outcome of the rehabilitation. The systems and methods can also apply an additional level of clinical oversight when a patient's progress is not improving. By combining the objective criteria with a patient's actual clinical data, a claims handler can more appropriately make an objective decision on a case-by-case basis.

6 Claims, 7 Drawing Sheets

PHYSICAL THERAPY PATIENT TREATMENT MONITORING SYSTEMS AND METHODS

CROSS-REFERENCE TO RELATED APPLICATIONS

This application claims priority to U.S. Provisional Patent Application Ser. No. 61/761,296, filed Feb. 6, 2013, entitled "Physical Therapy Patient Treatment Monitoring Systems and Methods," and U.S. Provisional Patent Application Ser. No. 61/739,251, filed Dec. 19, 2012, entitled "Physical Therapy Patient Treatment Monitoring Systems and Methods," both of which are incorporated by reference in their entirety.

BACKGROUND

Guideline management tools, such as Official Disability Guidelines (ODG), give a general overview of what a case should look like and, therefore, can only take a claims handler so far in their decision making process. The claims handler can use the ODG as a reference to identify a recommended course of action, but the claims handler must ultimately decide how to proceed in view of these recommendations and a treating physician's submitted plan, though the claims handler usually makes a referral based only on the rehabilitation order of the physician. As a result, the need for rehabilitation or continued care may be solely established by the physician, who initiates all subsequent requests. The physician's recommendations often ignore the established clinical guidelines in the ODG, which are widely accepted, but rarely acted upon, especially in the workers compensation industry. The claims handler then perpetuates a claim based on subjective criteria, thereby driving costs up and eliminating the ability to deliver a positive clinical outcome.

SUMMARY

It is desirable to achieve best in class outcomes for every component in the healthcare delivery process and to deliver them an objectively-based platform. The physical therapy treatment systems and methods described herein include an active utilization management (UM) program that can monitor the clinical efficacy of outpatient rehabilitation, including on-going physical therapy or occupational therapy. When a treating physician submits a claim, the systems and methods described herein can automatically apply a guideline for monitoring the pace of treatment and outcome of the rehabilitation. The systems and methods can also apply an additional level of clinical oversight when a patient's progress is not improving. By combining the objective criteria with a patient's actual clinical data, a claims handler can more appropriately make an objective decision on a case-by-case basis.

In one embodiment, a computer-implemented method for monitoring rehabilitation comprises receiving, by a server, a claim for rehabilitation of a patient; transmitting, by the server, a rehabilitation order to a therapist; receiving, by the server, a plan from the therapist for rehabilitation of the patient; comparing, by the server, the plan from the therapist with guidelines and normative values of treatment; and determining, by the server, a rehabilitation plan having an appropriate number of visits to the therapist based upon the comparison to accomplish the normative values.

In another embodiment, a computer-implemented method for managing a rehabilitation of a patient comprises determining, by the server, a rehabilitation plan having an appropriate number of visits to a therapist based on guidelines of treatment to accomplish desired normative values of a patient; receiving, by the server, a status of the patient during the rehabilitation plan; reassessing, by the server, rehabilitation progress of the patient on a periodic basis; and authorizing, by the server, a subset of a remaining number of visits to the therapist to accomplish the desired normative values.

Additional features and advantages of an embodiment will be set forth in the description which follows, and in part will be apparent from the description. The objectives and other advantages of the invention will be realized and attained by the structure particularly pointed out in the exemplary embodiments in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The methods, systems and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 2 illustrates a first screenshot according to an exemplary embodiment.

FIG. 3 illustrates a second screenshot according to an exemplary embodiment.

FIG. 4 illustrates a third screenshot according to an exemplary embodiment.

FIG. 5 illustrates a fourth screenshot according to an exemplary embodiment.

DETAILED DESCRIPTION

Various embodiments and aspects of the invention will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present invention.

The systems and methods described herein allow for a more appropriate management of rehabilitation treatment. For example, when a patient is injured, the patient visits a doctor. The doctor may request physical therapy for the patient's injury. So the doctor writes a prescription for physical therapy, e.g., three visits a week for four weeks (12 total visits). A claims handler receives the request and makes a referral the system described herein to arrange for physical therapy with a physical therapist in the network. The network physical therapist will see the patient and perform an initial evaluation. The physical therapist records baseline deficits and sends those to the system as part of a plan of care. The system can compare the baseline deficits and the physician's request to guidelines and norms for range of motion and strength to determine an appropriate plan of care.

Figure 1:
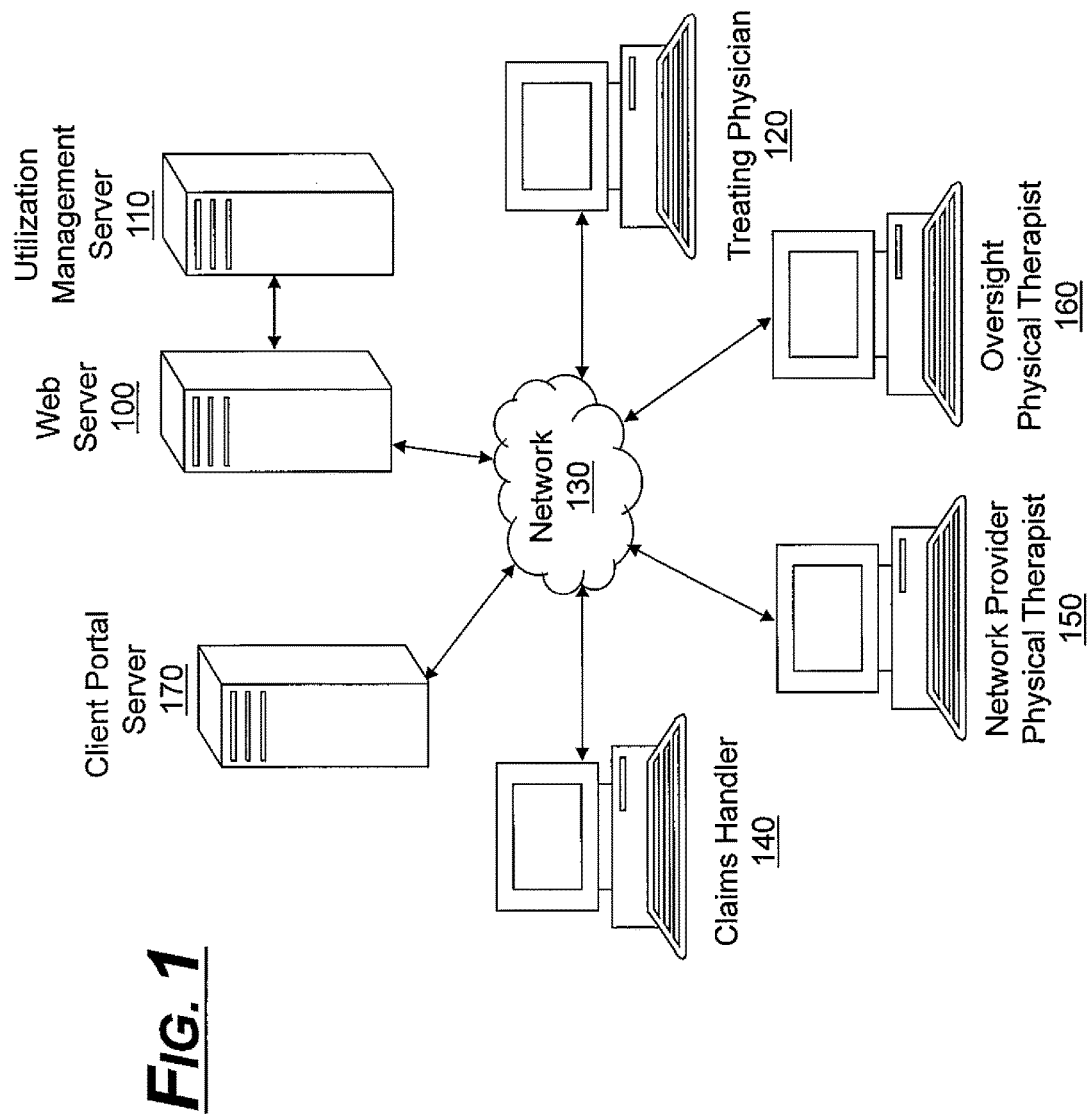
FIG. 1 illustrates a system overview according to an exemplary embodiment.

Referring to FIG. 1, an exemplary system overview is shown. A treating physician 120 examines a patient and submits a rehabilitation order through a network 130 to a claims handler 140. The network 130 can include any communication network, including the internet, telephone network, or other computer-based network. The claims handler 140, as described herein, can include the roles of an adjuster, case management personnel, and utilization review (UR) personnel. The physician 120 and the claims handler 140 can each communicate via a computing device, such as a personal computer, server, tablet computer, smart phone, mobile phone, or other computing system.

The claims handler 140 submits the rehabilitation order via the network 130 to a utilization management server 110 for order fulfillment. In this exemplary embodiment, the rehabilitation order is transmitted over the internet by submitting the information on a website, so the information is transmitted through a web server 100, which presents information for display on a web browser of the computing device of the claims handler 140 and processes information to and from the utilization management server 110. Although the utilization management server 110 is shown as a server, it is intended that the utilization management server 110 may be implemented as one or more servers and/or databases.

The claims handler 140 can submit the rehabilitation order to an outside entity (e.g., other network manager or an ancillary benefits manager (ABM)) for order fulfillment. As shown in the exemplary embodiment in FIG. 1, the rehabilitation order can be transmitted via the internet by transmitting the information of the rehabilitation order via network 130 to a client portal server 170. The client portal server 170 can host a website that presents a customer portal, whereby the client portal server 170 can present the customer portal and its information to be accessible by the claims handler 140 and the utilization management server 110. In this exemplary embodiment, the flow of information from and between the claims handler 140 and the utilization management server 110 will always pass via the network 130 through the client portal server 170, but does not affect the functionality of the utilization management server 110. The client portal server 170 can serve as a centralized access point for providing and accessing customer information. In an alternative embodiment, the claims handler 140 can communicate directly with the utilization management server 110 via the network 130 without transmitting through a client portal server 170, and the functionality of the client portal server 170 can be incorporated into another component of the system, or the information and the rehabilitation order can be transmitted without the use of a customer portal or centralized access point. In this description of the exemplary embodiment, it is intended that transmissions between the claims handler 140 and the utilization management server 110 may or may not proceed through a client portal server 170.

The utilization management server 110 transmits the rehabilitation order to a network provider physical therapist 150 for an initial evaluation of the patient. Although described as a network provider physical therapist, it is intended that the physical therapist is not necessarily required to be a part of a provider network associated with the utilization management server 110. The physical therapist 150 can communicate via a computing device, such as a personal computer, server, tablet computer, smart phone, mobile phone, or other computing system. The physical therapist 150 records baseline deficits of the patient, writes the rehabilitation plan, and submits the plan to the utilization management server 110 for comparison to the guidelines and norms (e.g., ROM and strength).

The utilization management server 110 processes the rehabilitation plan submitted by the physical therapist 150 to determine an appropriate number of visits, length of treatment, frequency of visits, or other characteristics of the treatment. The utilization management server 110 receives patient information, including demographics of the patient and information about the patient's condition from the treating physician 120 for the patient's initial evaluation. The utilization management server 110 also uses the current, latest, or future version of the International Classification of Diseases (e.g., ICD-9, ICD-10), along with established and widely recognized clinical treatment guidelines and normative values for one or more conditions of a patient, including range of motion (ROM) and strength. The utilization management server 110 identifies the appropriate treatment guidelines based upon the ICD, and compares the patient information to those treatment guidelines to determine a rehabilitation plan that will achieve the goals of normative ROM and strength. Unlike conventional recommendations, the utilization management server 110 removes the subjectivity from the decision making process. Accordingly, when the claims handler 140 receives a patient's file, the claims handler 140 can confidently address requests for authorization of continued care if there is clinical need based upon the clinical results and best practices guidelines.

Figure 2:
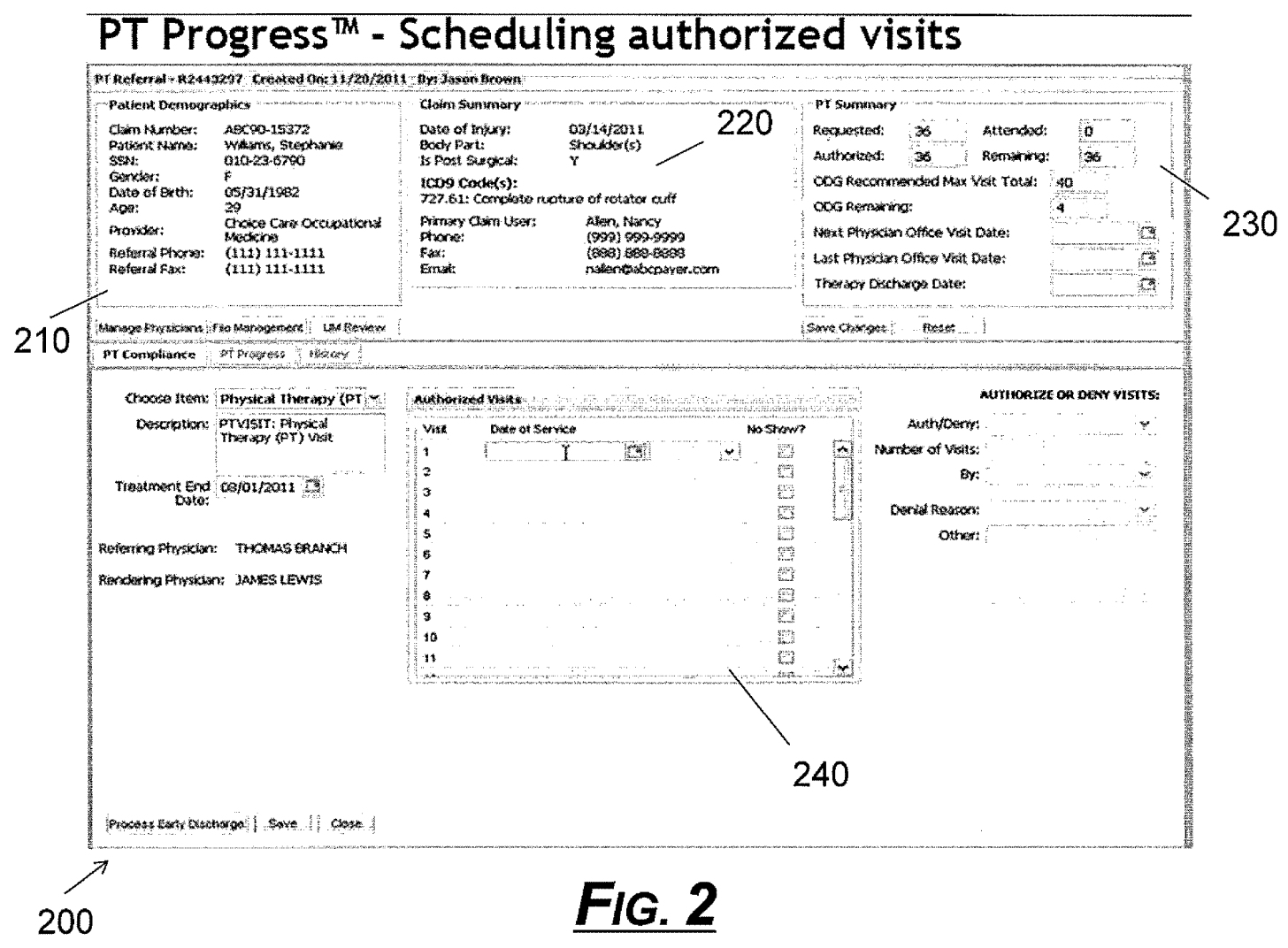

Referring to FIG. 2, a graphical user interface 200 is shown with patient demographics, whereby the injured patient's ICD-9 is linked or associated with the recommended guideline from the ODG to determine a maximum number of visits needed for rehabilitation. An upper left box 210 provides identifying information and demographics about the patient, including claim number, patient name, social security number, gender, date of birth, age, provider, referral phone number, and referral fax number. An upper middle box 220 depicts the ICD-9 information, including date of injury, injured body part, whether post surgical, ICD9 code(s), primary claim user, phone number, fax, and email. An upper right box 230 depicts information about the requested visits, authorized visits, attended visits, remaining visits, ODG recommended visits, ODG remaining visits, next physician office visit date, last physician office visit date, and therapy discharge date. A log of authorized visits 240 allows entry of and stores information about each visit including the date of service and whether the patient was a "no show." The graphical user interface may be presented on a web browser of a claims adjuster or network provider physical therapist to complete or view these fields.

The utilization management server 110 can objectively determine an optimal number of visits for the patient to achieve the desired goals. By monitoring progress towards those goals, the utilization management server 110 can achieve two benefits. First, if rehabilitation is proceeding slower and will require more visits, the utilization management server 110 can request an intervention to determine the necessity of the additional visits or inquire about other issues affecting treatment. Second, if the patient is progressing more quickly than planned, then the utilization management server 110 can determine that after the patient achieves those goals, the remaining visits are unnecessary. The claims handler 140 can benefit from only providing services for the necessary visits and can eliminate costs from additional visits where the patient has already achieved the desired goals. This approach may be contrary to many businesses in the rehabilitation industry that are compensated based upon a number of visits, where is little incentive to reduce the number of visits.

The utilization management server 110 can objectively track a patient's baseline deficits from their initial evaluation through their discharge from physical therapy. The utilization management server 110 can periodically (e.g., after every sixth visit) reassess a patient's progress (e.g., advancement to normative goals for ROM and strength for articulations identified by the guidelines). The latest visit can be compared to one or more of a previous visit (e.g., compare visit #12 to visit #11) or a visit from the last assessment (e.g., compare visit #12 to visit #6 based upon an assessment every six visits). Accordingly, the utilization management server 110 can determine whether the patient's condition is improving and can substantiate the need for additional care.

Figure 3:
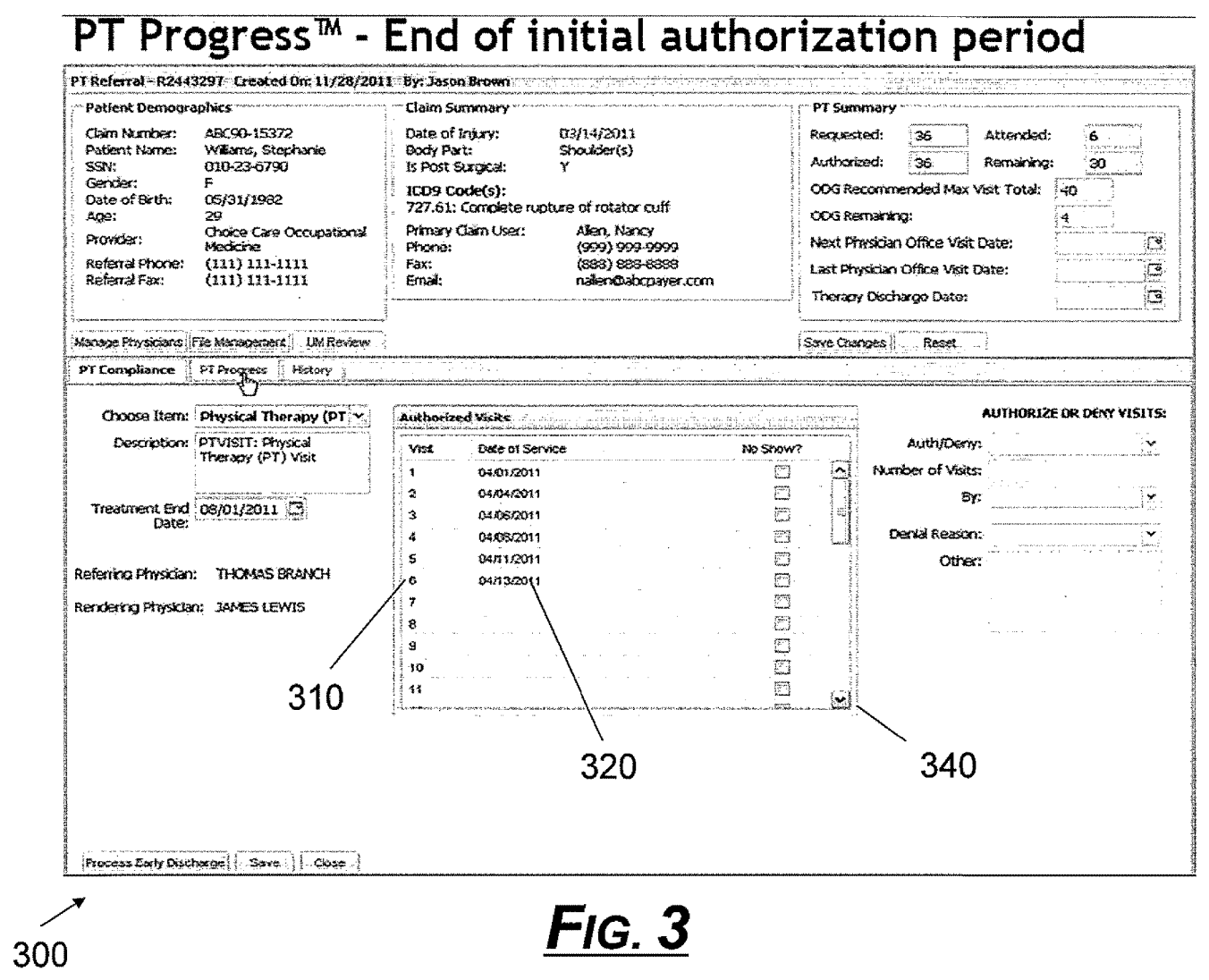

Referring to FIG. 3, a graphical user interface 300 is shown whereby the patient has attended six visits with the physical therapist, as shown in a log of authorized visits 340. Dates 310 for each visit 320 are shown as well. The graphical user interface may be presented on a web browser of a claims adjuster or network provider physical therapist.

Figure 4:
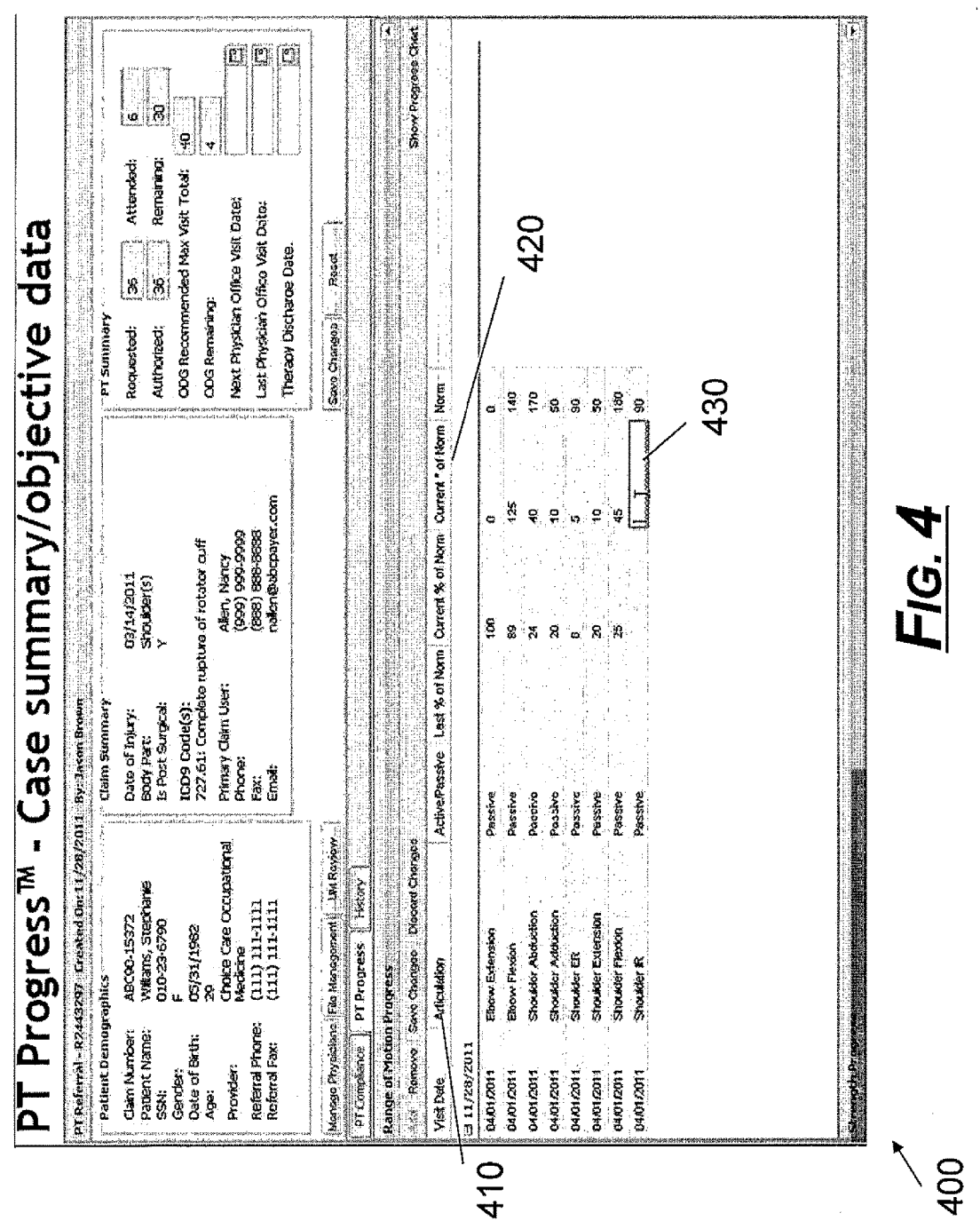

Referring to FIG. 4, a graphical user interface 400 is shown for tracking a patient's progress. Based on the IDC and guidelines, the user interface 400 will present each articulation 410 for monitoring and prompt the physical therapist for an updated entry of ROM and strength for that articulation. For example, based on an IDC-9 of 727.61 (complete rupture of the rotator cuff), the graphical user interface will automatically present articulations 410 including elbow extension, elbow flexion, shoulder abduction, shoulder ER, should extension, shoulder flexion, and shoulder IR. The network provider physical therapist can enter the ROM or strength value or percentage 420 in an appropriate field, e.g., field 430, and the user interface will compare this entry to the norm. The utilization management server 110 can be updated to transaction from an IDC-10 platform from an IDC-9 platform. Also, the utilization management server 110 can be automatically updated when recommended guideline visits change for a particular diagnosis. Some guidelines may vary by state or jurisdiction, so the utilization management server 110 can account for the variances in jurisdictions and update each jurisdiction accordingly.

The utilization management server 110 can monitor the patient's progress based upon the inputted information. If the patient's progress is not improving, demonstrating a plateau, regressing, or is otherwise projected to be unsuccessful within the recommended amount of visits, the utilization management server 110 will identify the such a condition that activates a trigger or flag for that patient. Based upon this trigger, the utilization management server 110 will transmit a notification to an oversight physical therapist 160 for clinical oversight and review. The oversight physical therapist 160 can communicate via a computing device, such as a personal computer, server, tablet computer, smart phone, mobile phone, or other computing system.

By linking the ICD-9 with the guideline recommendations for the necessary visits of physical therapy, the utilization management server 110 can determine on the initial evaluation or any subsequent visit whether a request for physical therapy is excessive or outside the norm. In an example, a patient has an injured shoulder. The diagnosis of the treating physician 120 is a complete rupture of their rotator cuff muscle with ICD-9 of 727.61. The guidelines recommend 40 visits for this diagnosis. The utilization management server 110 can collect all of this data. When the requested number of visits exceeds 40, the utilization management server 110 can generate a flag to trigger peer-to-peer intervention. So if the network provider physical therapist 150 requests 66 visits of physical therapy, the case is flagged for a first peer-to-peer intervention communication. After a sixth visit, the utilization management server 110 will reassess the data entered by the physical therapist 150 for ROM and strength to see if the patient regresses, remains the same, or improves. If the patient remains the same or regresses, the utilization management server 110 will trigger another peer-to-peer intervention communication.

The oversight physical therapist 160 receives the notification and can initiate a peer-to-peer intervention with the physical therapist 150. The peer-to-peer intervention can be a communication through network 130, and can take the form of a telephone call, video conference, chat, video chat, email, or other communication. During this communication, the oversight physical therapist 160 can determine why sufficient progress is not being made, and the oversight physical therapist 160 can enter a recommendation, which is transmitted to the utilization management server 110. The utilization management server 110 will transmit the recommendation to the claims handler 140 for adjustment of the patient's rehabilitation plan. In one alternative embodiment, the oversight physical therapist 160 can correspond directly with the claims handler 140 through the network 130, such as by email correspondence. If the claims handler 140 decides to adjust the rehabilitation plan, the claims handler 140 will submit the revised plan to the utilization management server for updating and monitoring of the new plan. During this process, recommendations and adjustments can also be transmitted to the treating physician 120 via email, fax, or other correspondence method.

The oversight physical therapist 160 receives from the utilization management server 110 the patient's data in comparison to the established norms for ROM and strength. This oversight is a feature that is not present in conventional treatment, whereby a physical therapist and/or claims handler rely entirely on the requests of the treating physician.

Figure 5:
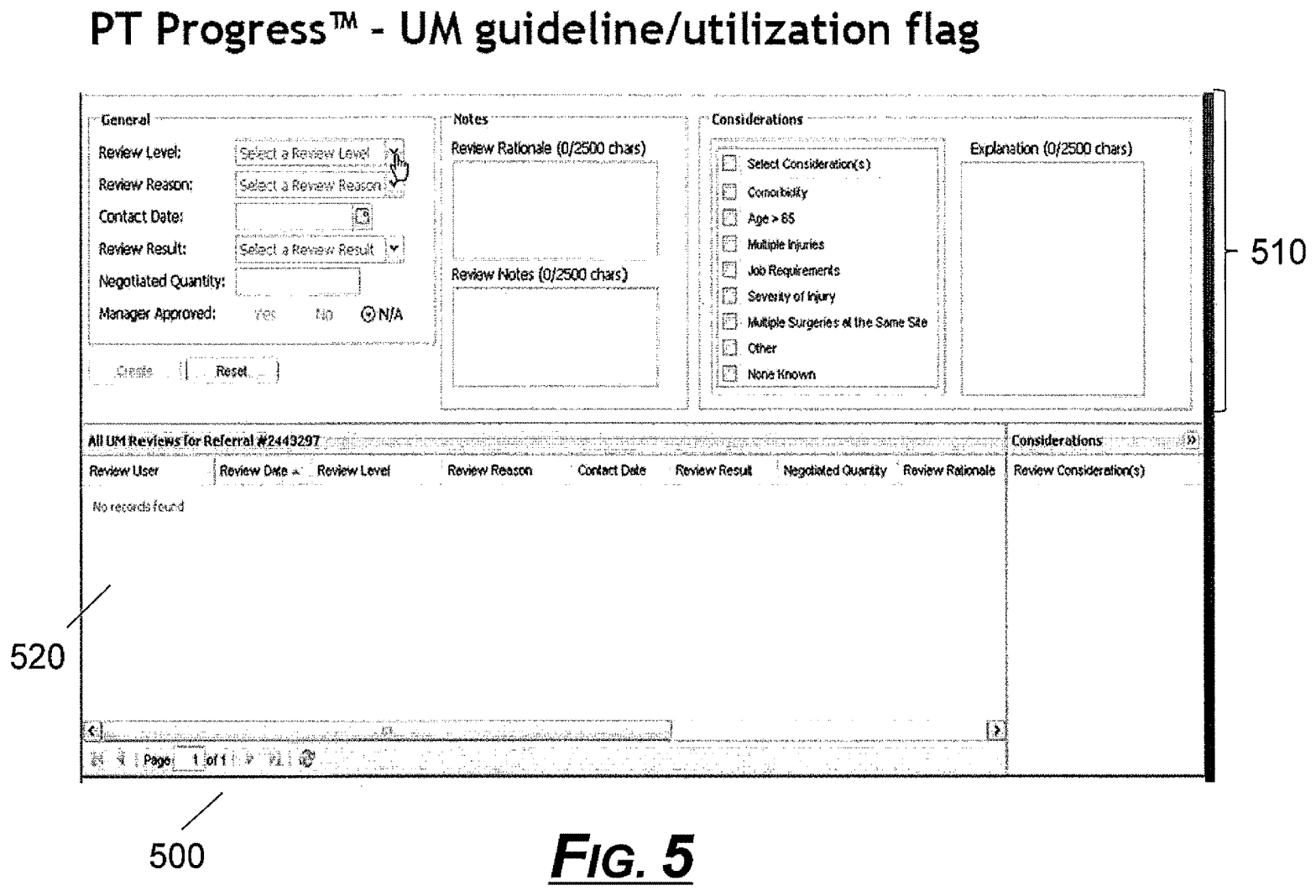

Referring to FIG. 5, a graphical user interface 500 is shown to create and manage a database record that can record findings and conclusions in a peer-to-peer intervention between an oversight physical therapist and a network provider physical therapist. The oversight physical therapist can input information into an upper portion 510 the graphical user interface 500, including a review level, review reason, contact date, review result, negotiated quantity, manager approved, review rationale, review notes, considerations, and explanation. A table 520 can also display previous reviews.

Figure 6A:
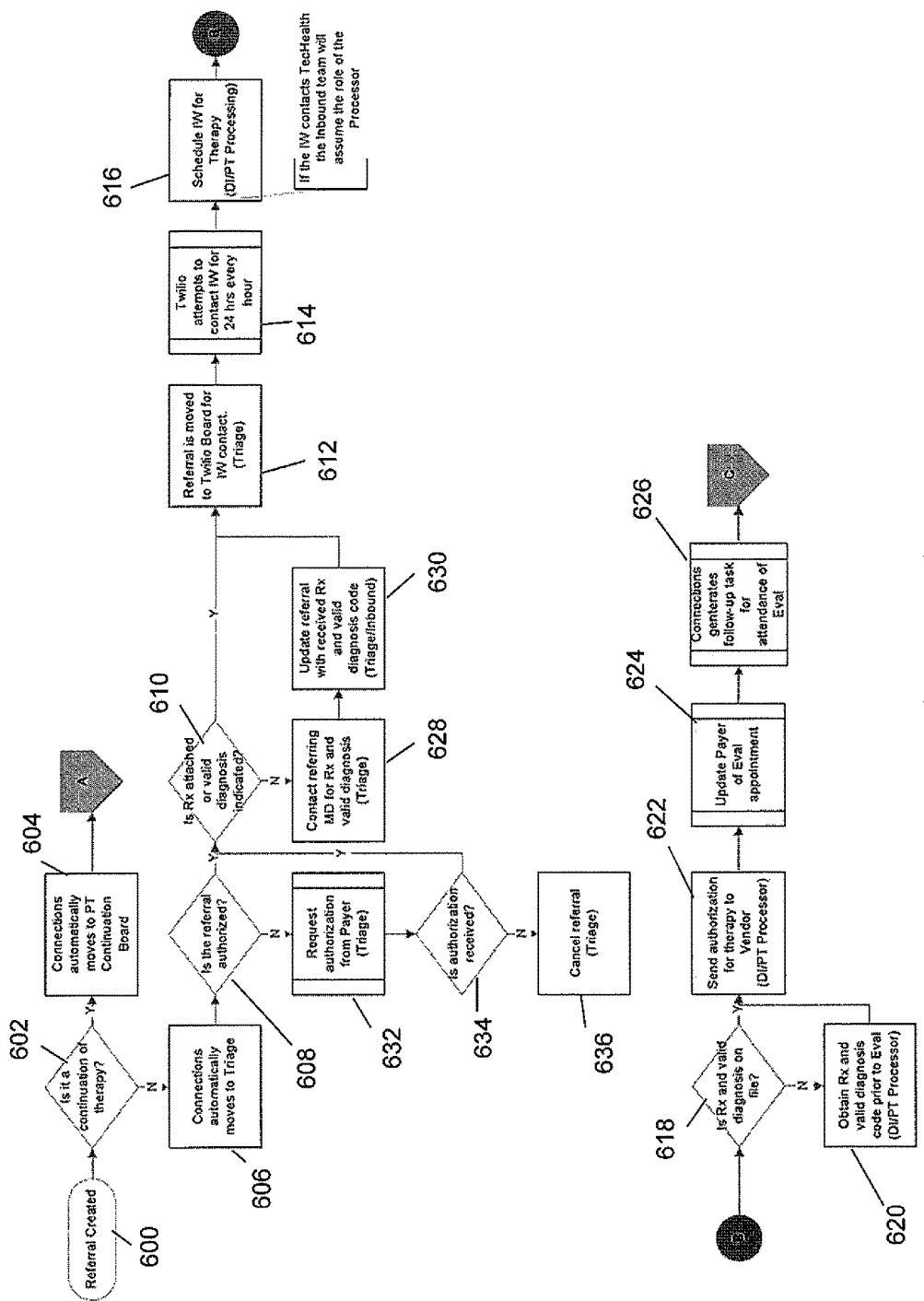
FIGS. 6A and 6B illustrate a method according to an exemplary embodiment.
Figure 6B:
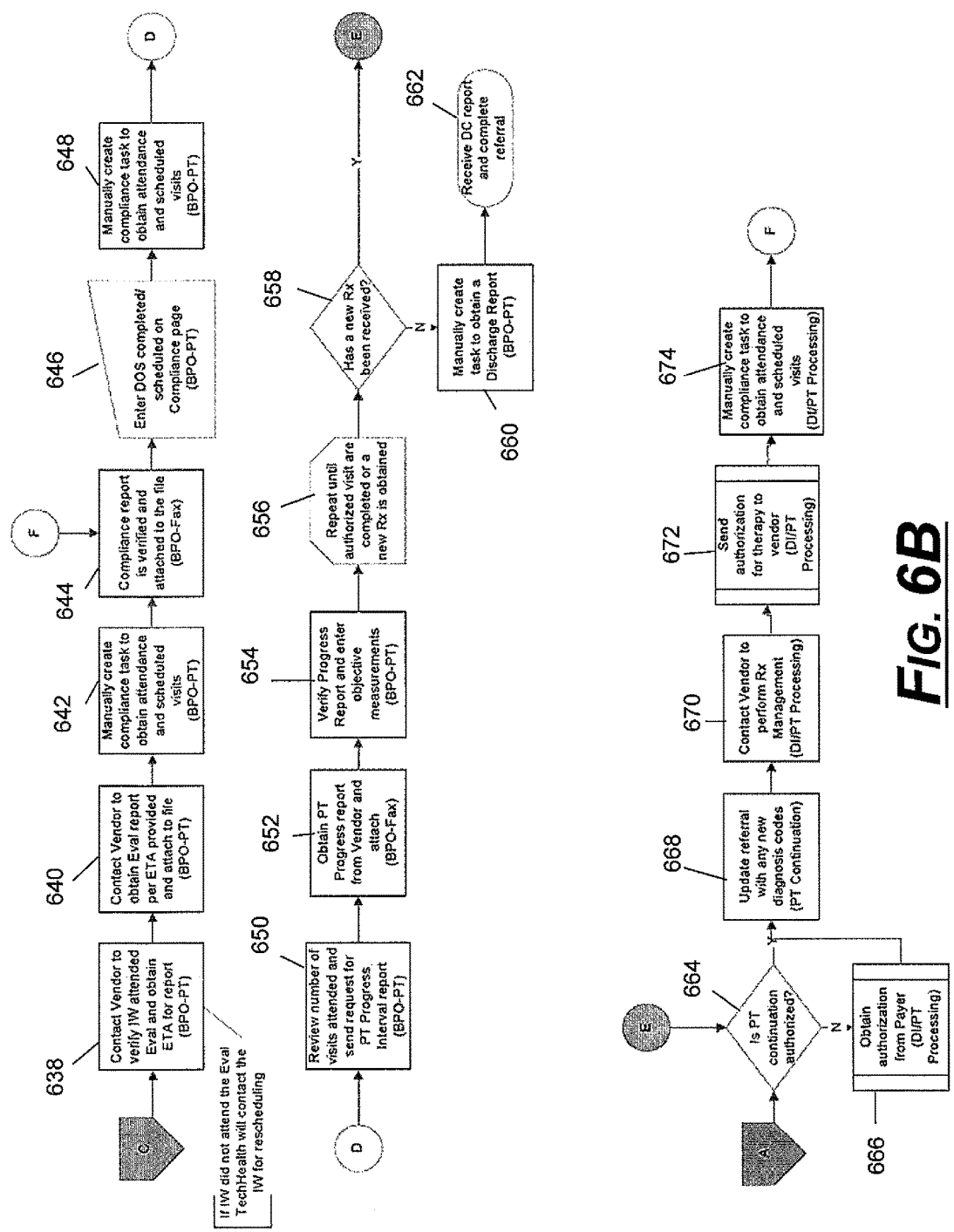

An exemplary method is shown in FIGS. 6A and 6B. This exemplary method is carried out by the utilization server shown in FIG. 1. In step 600, a referral is created. In step 602, it is determined whether it is a continuation of therapy. If so, in step 604, a software program embodied on and executed by the server (the software is commercially referred to as "Connections") automatically moves to a continuation board. When an injured worker has already received physical therapy treatment, the injured worker may receive more physical therapy sessions, which would be managed by the continuation board. The process then continues in step 664.

If the referral is not a continuation of therapy, then, in step 606, the Connections software automatically moves to triage, which is division that handles new referrals to verify that the referral has the required information fro processing. In step 608, it is determined whether the referral is authorized. If so, in step 610, it is determined whether a prescription is attached or a valid diagnosis is indicated. If so, in step 612, a referral is moved to an automatic redialer, such as Twillio, for injured worker contact. The automatic redialer can call automatically call each number for each injured worker in each referral and transfer the call to a representative when a live person picks up the call. In step 614, Twillio attempts to contact the injured worker every hour for twenty-four hours. In step 616, the injured worker schedules therapy. The process then continues in step 618, where it is determined if the prescription is still valid and the diagnosis is on file. If not, in step 620, the prescription a valid diagnosis code is obtained prior to evaluation. If so, in step 622, authorization for therapy is sent to vendor. In step 624, the payer is updated of evaluation appointment. In step 626, connections generates follow-up task for attendance of evaluation. The process then continues in step 638. If the prescription is not attached or a valid diagnosis is not indicated, then in step 628, a referring doctor is contacted for a prescription and valid diagnosis. In step 630, the referral is updated with the received prescription and valid diagnosis code.

If the referral is not authorized, in step 632, authorization is requested from the payer. In step 634, it is determined whether authorization is received. If so, the process proceeds to step 610. If not, in step 636, the referral is canceled.

In step 638, a vendor is contacted to verify that the injured worker attended the evaluation and obtain an estimated time of arrival for a report. In step 640, the vendor is contacted to obtain the evaluation report per the estimated time of arrival and attach to the file. In step 642, a compliance task is created to obtain attendance and scheduled visits. In step 644, a compliance report is verified and attached to the file. In step 646, the date of service is entered as completed/scheduled on the compliance page. In step 648, a compliance task is created to obtain attendance and scheduled visits. The process proceeds to step 650, and the number of visits attended is reviewed and a request is sent for a physical therapy progress interval report. In step 652, a physical therapy progress report is obtained from the vendor and attached. In step 654, the progress report is verified and objective measurements are entered. In step 656, it is repeated until authorized visits are completed or a new prescription is obtained. In step 658, it is determined whether a new prescription has been received. If so, the process proceeds to step 664. If not, in step 660, a task is created to obtain a discharge report. In step 662, a discharge report is received and referral is completed.

In step 664, it is determined whether the physical therapy continuation is authorized. If not, in step 666, authorization is obtained from the payer. If so, in step 668, the referral is updated with any new diagnosis codes. In step 670, the vendor is contacted to perform prescription management. In step 672, authorization for therapy is sent to the vendor. In step 674, a compliance task is created to obtain attendance and scheduled visits. The process proceeds to step 644.

In one example, a patient suffers a shoulder injury and sees a treating physician. On day 1, his initial evaluation, he presents with weakness and limited mobility. The treating physician records those two components and submits them to the claims handler, who in turn submits them to the utilization management server. These baseline data points are compared to what is known to be the normal values for each component, which in this case would be range of motion (ROM) and strength. The normal values for ROM and strength are known to all licensed practitioners. In this example, normative data generated by the American Academy of Orthopaedic Surgeons (AAOS) can be embedded into the system. A physical therapist can enter the patient's individual values for strength and ROM at each visit or each periodic visit. This data is unknown to others not involved in the treatment of this particular patient. No other system compares this data to the known normative values to track progress and pace of treatment. As a result, a claims handler can determine with specificity what an individual patient may or may not need clinically to be restored to full function.

The utilization management server 110 can generate reports showing the savings that can be derived from this system. In one example, the utilization management server 110 can generate a report that identifies how many patients were treated until discharge with an amount of visits below the amount offered by the recommended guidelines. No other system can determine a recommended number of visits for a particular condition, monitor the progress through each visit until discharge, determine whether an adjustment should be made to treatment or the number of visits, and determine a number of requested visits versus the number actually required.

The functionality described herein can be implemented by numerous modules or components that can perform one or multiple functions. Each module or component can be executed by a computer, such as a server, having a non-transitory computer-readable medium and processor. In one alternative, multiple computers may be necessary to implement the functionality of one module or component.

Unless specifically stated otherwise as apparent from the following discussion, it is appreciated that throughout the description, discussions utilizing terms such as "processing" or "computing" or "calculating" or "determining" or "displaying" or the like, can refer to the action and processes of a data processing system, or similar electronic device, that manipulates and transforms data represented as physical (electronic) quantities within the system's registers and memories into other data similarly represented as physical quantities within the system's memories or registers or other such information storage, transmission or display devices.

The exemplary embodiments can relate to an apparatus for performing one or more of the functions described herein. This apparatus may be specially constructed for the required purposes, or it may comprise a general purpose computer selectively activated or reconfigured by a computer program stored in the computer. Such a computer program may be stored in a machine (e.g. computer) readable storage medium, such as, but is not limited to, any type of disk including floppy disks, optical disks, CD-ROMs and magnetic-optical disks, read only memories (ROMs), random access memories (RAMs) erasable programmable ROMs (EPROMs), electrically erasable programmable ROMs (EEPROMs), magnetic or optical cards, or any type of media suitable for storing electronic instructions, and each coupled to a bus or other communication device.

The exemplary embodiments described herein are described as software executed on at least one server, though it is understood that embodiments can be configured in other ways and retain functionality. The embodiments can be implemented on known devices such as a personal computer, a special purpose computer, cellular telephone, personal digital assistant ("PDA"), a digital camera, a digital tablet, an electronic gaming system, a programmed microprocessor or microcontroller and peripheral integrated circuit element(s), and ASIC or other integrated circuit, a digital signal processor, a hard-wired electronic or logic circuit such as a discrete element circuit, a programmable logic device such as a PLD, PLA, FPGA, PAL, or the like. In general, any device capable of implementing the processes described herein can be used to implement the systems and techniques according to this invention.

It is to be appreciated that the various components of the technology can be located at distant portions of a distributed network and/or the Internet, or within a dedicated secure, unsecured and/or encrypted system. Thus, it should be appreciated that the components of the system can be combined into one or more devices or co-located on a particular node of a distributed network, such as a telecommunications network. As will be appreciated from the description, and for reasons of computational efficiency, the components of the system can be arranged at any location within a distributed network without affecting the operation of the system. Moreover, the components could be embedded in a dedicated machine.

Furthermore, it should be appreciated that the various links connecting the elements can be wired or wireless links, or any combination thereof, or any other known or later developed element(s) that is capable of supplying and/or communicating data to and from the connected elements. The term module as used herein can refer to any known or later developed hardware, software, firmware, or combination thereof that is capable of performing the functionality associated with that element. The terms determine, calculate and compute, and variations thereof, as used herein are used interchangeably and include any type of methodology, process, mathematical operation or technique.

The embodiments described above are intended to be exemplary. One skilled in the art recognizes that there are numerous alternative components and embodiments that may be substituted for or included in the particular examples described herein and such additions or substitutions still fall within the scope of the invention.

What is claimed is:

1. A method for monitoring rehabilitation, the method comprising:
    storing, by a server, a first content in a first record of a database and a second content in a second record of the database, wherein the first content is created via a first instance of an application running on an operating system of a physician client interfacing with the server over a network and includes a rehabilitation order for a patient associated with the physician client, wherein the second content includes an updatable standard comprising at least one of an objective guideline of a treatment or an objective normative value of treatment;
    in response to receiving, by the server, over the network, a request from a second instance of the application running on an operating system of a claim handler client interfacing with the server after the storing;
        retrieving, by the server, the first content from the first record,
        generating, by the server, a first page of a graphical user interface such that the first page contains the first content retrieved from the first record and such that the first page is able to receive a therapist input into a third instance of the application running on an operating system of a therapist client, and
        transmitting, by the server, over the network, the first page to the therapist client such that the first page, including the first content, is presented via the third instance;
    determining, by the server, whether the first content including the rehabilitation order does not satisfy a predetermined condition;
    determining, by the server, whether the first content including the rehabilitation order is authorized based on the predetermined condition not being satisfied;
    determining, by the server, whether the first content including the rehabilitation order includes a file based on the first content including the rehabilitation order being authorized;
    moving, by the server, the first content including the rehabilitation order including the file to an automatic redialer sourced via an application programming interface (API) that is hosted remote from the server, wherein the automatic redialer sourced via the API is configured to periodically make a call to each patient telephone number within the first content including the rehabilitation order including the file and transfer the call to a predetermined phone number when a live person picks up the call, wherein the predetermined number is associated with a representative client, wherein the patient is the live person;
    scheduling, by the server, over the network, based on the call, a session for the patient based on the first content including the rehabilitation order including the file from a fourth instance of the application running on an operating system of the representative client interfacing with the server during the call;
    in response to receiving, by the server, over the network, a message for the session from the therapist client;
        extracting, by the server, a third content from the message, wherein the third content includes a plan for a rehabilitation of the patient that includes the session, wherein the message is created based on the therapist input via the third instance as the first content is presented on the first page in the third instance,
        retrieving, by the server, the second content from the second record,
        comparing, by the server, the third content against the second content,
        creating, by the server, based on the comparing, a fourth content, wherein the fourth content includes an appropriate number of visits including the session to a therapist associated with the therapist client in order to achieve at least one of a normative range of motion or a strength of the patient,
        generating, by the server, a second page of the graphical user interface such that the second page contains the fourth content, and
        transmitting, by the server, the over the network, the second page to the claim handler client such that the second page, including the fourth content, is presented via the second instance,
    wherein the server is a first server, wherein the claim handler client, the representative client, and the therapist client communicate with the first server through a second server distinct from the first server, wherein the second server presents a network-based client portal into which the claim handler client and the therapist client and the representative client are logged in concurrently via the second instance and the third instance and the fourth instance respectively.

2. The method according to claim 1, further comprising:
determining, by the server, a length of treatment of the patient based on the comparing, wherein the plan for the rehabilitation comprises the length of treatment of the patient.

3. The method according to claim 1, further comprising:
determining, by the server, a frequency of visits for the patient based on the comparing, wherein the plan for the rehabilitation comprises the frequency of visits for the patient.

4. The method according to claim 1, wherein the creating further comprises using data representative of a demographic of the patient sourced from the first content.

5. The method according to claim 1, wherein the creating further comprises using data representative of an initial evaluation of the patient sourced from the first content.

6. A method for monitoring rehabilitation, the method comprising:
storing, by a server, a first content in a first record of a database and a second content in a second record of the database, wherein the first content is created via a first instance of an application running on an operating system of a physician client interfacing with the server over a network and includes a rehabilitation order for a patient associated with the physician client, wherein the second content includes an updatable standard comprising at least one of an objective guideline of a treatment or an objective normative value of treatment;
in response to receiving, by the server, over the network, a request from a second instance of the application running on an operating system of a claim handler client interfacing with the server after the storing:
retrieving, by the server, the first content from the first record,
generating, by the server, a first page of a graphical user interface such that the first page contains the first content retrieved from the first record and such that the first page is able to receive a therapist input into a third instance of the application running on an operating system of a therapist client, wherein the third instance is configured for a peer-to-peer session, and
transmitting, by the server, over the network, the first page to the therapist client such that the first page, including the first content, is presented via the third instance;
in response to receiving, by the server, over the network, a message from the therapist client:
extracting, by the server, a third content from the message, wherein the third content includes a plan for a rehabilitation of the patient, wherein the message is created based on the therapist input via the third instance as the first content is presented on the first page in the third instance,
retrieving, by the server, the second content from the second record,
comparing, by the server, the third content against the second content,
creating, by the server, based on the comparing, a fourth content, wherein the fourth content includes an appropriate number of visits to a therapist associated with the therapist client in order to achieve at least one of a normative range of motion or a strength of the patient,
generating, by the server, a second page of the graphical user interface such that the second page contains the fourth content, and
transmitting, by the server, the over the network, the second page to the claim handler client such that the second page, including the fourth content, is presented via the second instance;
comparing, by the server, the appropriate number of visits in the fourth content against a threshold sourced from at least one of the objective guideline of the treatment or the objective normative value of treatment in the second content;
generating, by the server, a flag based on the threshold being satisfied;
associating, by the server, the flag with the appropriate number of visits in the fourth content;
reading, by the server, the flag as associated with the appropriate number of visits in the fourth content; and
initiating, by the server, over the network, based on the flag, the peer-to-peer session between the third instance of the application running on the operating system of the therapist client and a fourth instance of the application running on an operating system of an oversight therapist client, wherein the peer-to-peer session includes at least one of a video content or an audio content, wherein the peer-to-peer session is associated with the appropriate number of visits in the fourth content.

* * * * *